United States Patent
Karrer

Patent Number: 4,766,152
Date of Patent: Aug. 23, 1988

[54] OXIME DERIVATIVES

[75] Inventor: Friedrich Karrer, Zofingen, Switzerland

[73] Assignee: Ciba-Geigy Corporation, Ardsley, N.Y.

[21] Appl. No.: 858,619

[22] Filed: May 1, 1986

[30] Foreign Application Priority Data

May 2, 1985 [CH] Switzerland .......................... 1868/85
Jun. 4, 1985 [CH] Switzerland .......................... 2364/85
Mar. 21, 1986 [CH] Switzerland .......................... 1144/86

[51] Int. Cl.$^4$ ............................................. A61K 31/15
[52] U.S. Cl. ................................... 514/640; 564/254; 564/255; 564/256; 71/121; 71/100; 71/98
[58] Field of Search .................. 564/254, 255, 256; 514/640; 71/121

[56] References Cited

U.S. PATENT DOCUMENTS

4,514,406  0/1985  Ohsumi et al. ........................ 514/352

FOREIGN PATENT DOCUMENTS

3220524  12/1983  Fed. Rep. of Germany ...... 564/256
246361  12/1985  Japan ..................................... 564/256

OTHER PUBLICATIONS

Derwent, 84-267354/43-J59164-702-A, 1983.
Derwent, 84-266715/43-J59163-302-A, 1983.
Derwent, 84-266756/43-J59163/360-A, 1983.
Derwent, 84-267391/43-J59164/761-A, 1983.
Recent Progress in Insecticide Chemistry, Cambridge, Sep. 1984–T. Ohsumi et al.

*Primary Examiner*—James H. Reamer
*Attorney, Agent, or Firm*—Kevin T. Mansfield; Edward McC. Roberts

[57] ABSTRACT

The present invention relates to novel oximes of the formula

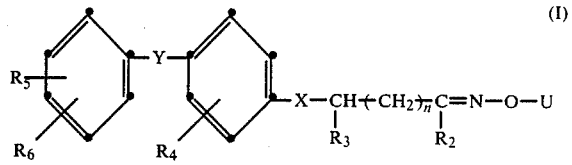

(I)

wherein
U is one of the radicals

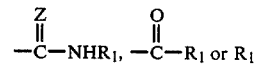

and
$R_1$ is $C_1$-$C_6$alkyl, $C_2$-$C_5$alkenyl, $C_3$monohaloalkenyl, $C_3$-$C_5$alkynyl, $C_3$-$C_6$cycloalkyl, $C_2$-$C_5$alkoxyalkyl, $C_2$-$C_5$alkylthioalkyl, or benzyl, which is unsubstituted or substituted at the nucleus,
$R_2$ and $R_3$ are each independently of the other hydrogen or $C_1$-$C_3$alkyl,
$R_4$, $R_5$ and $R_6$ are each independently of one another hydrogen, halogen, $C_1$-$C_4$alkyl, $C_2$-$C_4$haloalkyl, $C_1$-$C_4$alkoxy, $C_1$-$C_4$haloalkoxy or nitro,
n is 0 or 1,
X is oxygen, sulfur or

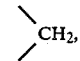

Y is oxygen, sulfur

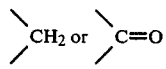

and
Z is oxygen or sulfur;

with the proviso that X and Y are not simultaneously oxygen and/or at least one of the radicals $R_4$, $R_5$ and $R_6$ has a meaning other than hydrogen if $R_1$ is a $C_1$-$C_3$alkyl group; to the preparation of said oxime derivatives and to the use thereof in pest control, in particular as ovicides against insects and representatives of the order Acarina.

18 Claims, No Drawings

OXIME DERIVATIVES

The present invention relates to oxime derivatives, to the preparation thereof and to the use thereof in pest control.

The oxime derivatives (oxime carbamates, oxime esters and oxime ethers) of this invention have the formula

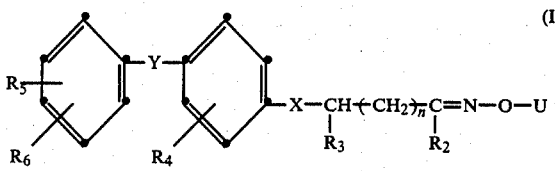

wherein
U is one of the radicals

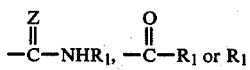

and
$R_1$ is $C_1$-$C_6$alkyl, $C_2$-$C_5$alkenyl, $C_3$monohaloalkenyl, $C_3$-$C_5$alkynyl, $C_3$-$C_6$cycloalkyl, $C_2$-$C_5$alkoxyalkyl, $C_2$-$C_5$alkylthioalkyl, or benzyl, which is unsubstituted or substituted at the nucleus,
$R_2$ and $R_3$ are each independently of the other hydrogen or $C_1$-$C_3$alkyl,
$R_4$, $R_5$ and $R_6$ are each independently of one another hydrogen, halogen, $C_1$-$C_4$alkyl, $C_2$-$C_4$haloalkyl, $C_1$-$C_4$alkoxy, $C_1$-$C_4$haloalkoxy or nitro,
n is 0 or 1,
X is oxygen, sulfur or

Y is oxygen, sulfur

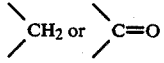

and
Z is oxygen or sulfur;
with the proviso that X and Y are not simultaneously oxygen and/or at least one of the radicals $R_4$, $R_5$ and $R_6$ has a meaning other than hydrogen if $R_1$ is a $C_1$-$C_3$alkyl group.

Within the scope of the present invention, halogen is fluorine, chlorine, bromine or iodine, preferably fluorine or chlorine.

The invention also relates to the possible isomers of the compounds of formula I.

The alkyl, alkoxy, haloalkyl, haloalkoxy, alkoxyalkyl, alkylthioalkyl, alkenyl and alkynyl groups may be straight chain or branched. Examples of such groups are, inter alia, methyl, methoxy, methoxymethyl, methylthiomethyl, difluoromethoxy, ethyl, ethoxy, 2-fluoroethoxy, 1,1,2,2-tetrafluoroethyl, pentafluoroethyl, 1,1,2,2-tetrafluoroethoxy, pentafluoroethoxy, propyl, isopropyl, n-butyl, n-pentyl, n-hexyl and the isomers thereof, vinyl, 1-propen-3-yl and 1-propynyl.

Preferred cycloalkyl groups $R_1$ are cyclopentyl and cyclohexyl.

Preferred substituents of the benzyl group $R_1$ are halogen, $C_1$-$C_4$alkyl, $C_1$-$C_4$alkoxy, $C_1$-$C_4$alkylthio or $C_1$-$C_4$haloalkyl.

Preferred compounds of formula I of the present invention are those wherein:
$R_1$ is $C_1$-$C_6$alkyl, $C_2$-$C_5$alkenyl, $C_3$chloroalkenyl, $C_3$-$C_5$alkynyl, or benzyl which is unsubstituted or substituted at the nucleus,
$R_2$ and $R_3$ are each independently of the other hydrogen or methyl,
$R_4$, $R_5$ and $R_6$ are hydrogen,
n is 0 or 1,
X is oxygen, sulfur or

Y is oxygen or

and
Z is oxygen or sulfur.
Particularly preferred compounds of formula I are those wherein U is one of the radicals

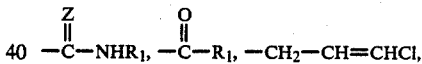

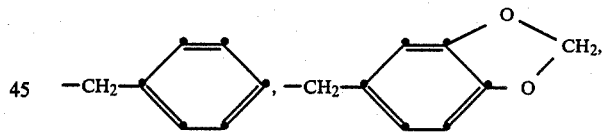

—$CH_2$—C≡CH or —$CH_2$—CH=$CH_2$,
and $R_1$, $R_2$, $R_3$, $R_4$, $R_5$, $R_6$, n, X, Y and Z are as defined above, with the proviso that Y and X are simultaneously oxygen and $R_2$ is methyl and/or that at least one of the radicals $R_4$, $R_5$ or $R_6$ has a meaning other than hydrogen if U is the —$CH_2$—CH=$CH_2$ radical.

To be singled out for particular mention on account of their biological significance are also the compounds of formula Ia of this invention

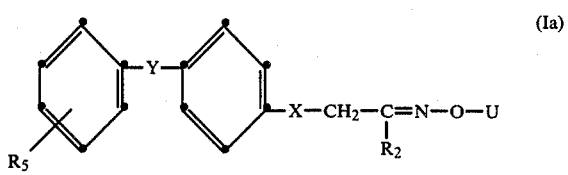

wherein
U is one of the radicals

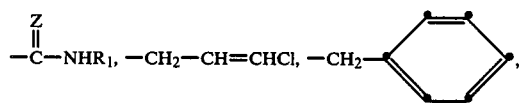

$R_1$ is $C_1$–$C_4$alkyl,
$R_2$ is hydrogen or methyl,
$R_5$ is hydrogen, halogen, methyl or trifluoromethyl,
X and Z are each independently of the other oxygen or sulfur, and
Y is oxygen or

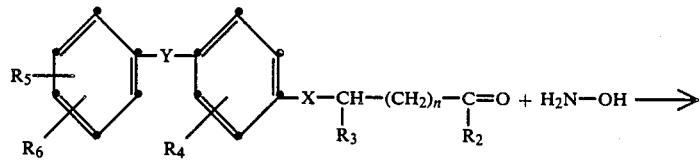

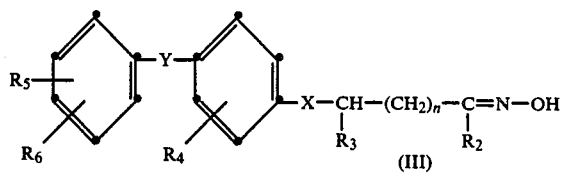

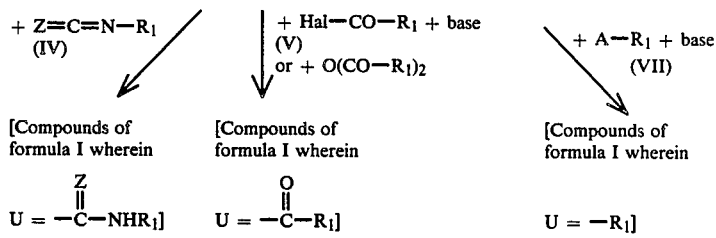

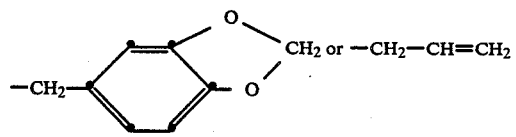

with the proviso that X and Y are simultaneously oxygen and $R_2$ is methyl and/or that $R_3$ has a meaning other than hydrogen if U is the —$CH_2$—CH=$CH_2$ radical.

The compounds of formula I or Ia can be prepared as follows by methods known per se:

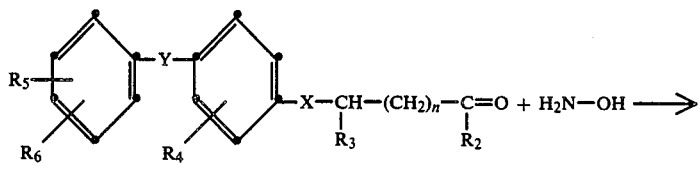

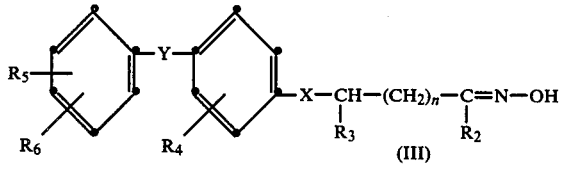

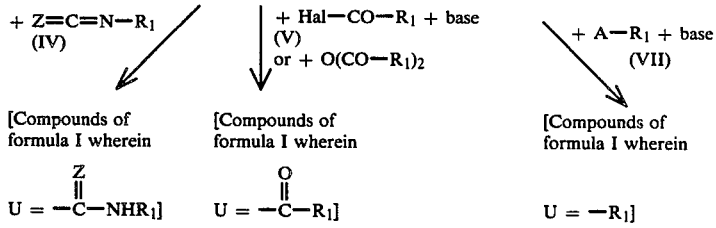

and $R_1$ to $R_6$, n, X, Y and Z in formulae II to VI have the meanings indicated above for formula I or Ia. Hal in formula V is a halogen atom, preferably chlorine. A in formula VII is a conventional leaving group, e.g. a halogen atom, preferably chlorine, or the mesyloxy or tosyloxy group. Suitable bases are in particular tertiary amines such as trialkylamines and pyridine, and also hydrides, hydroxides, oxides, carbonates and bicarbonates of alkali metals and alkaline earth metals, as well as alkali metal alcoholates, e.g. potassium tert-butylate and sodium methylate etc.

The above-described preparation of the compounds of this invention comprises first forming the oxime of formula III by reacting a carbonyl compound of formula II with hydroxylamine, and then reacting said oxime of formula III (a) with an isocyanate or isothiocyanate of formula IV or (b) with an acyl halide of formula V, in the presence of a base, or with an anhydride of formula VI or (c) with a compound of formula VII, in the presence of a base.

The process steps are carried out at a reaction temperature in the range from $-10°$ to $+150°$ C., usually from $+20°$ to $+80°$ C., under normal or increased pressure and preferably in an inert solvent or diluent. Examples of suitable solvents or diluents are ethers and ethereal compounds such as diethyl ether, diisopropyl ether, dioxane, 1,2-dimethoxyethane and tetrahydrofuran; amides such as N,N-dialkylated carboxamides; aliphatic, aromatic and halogenated hydrocarbons, in particular benzene, toluene, xylenes, chloroform and chlorobenzene; nitriles such as acetonitrile; dimethyl sulfoxide and ketones such as acetone and methyl ethyl ketone.

In order to prepare compounds of formula I or Ia wherein U is the radical $R_1$, a carbonyl compound of formula II, wherein $R_2$ to $R_6$, n, X and Y are as defined above, can also be reacted directly with a hydroxylamine hydrohalide derivative of formula VIII

$$[H_3\overset{\oplus}{N}-O-R_1]Hal^{\ominus} \qquad (VIII)$$

in the presence of a base, e.g. an alkali metal acetate, in which formula VIII the radical $R_1$ is as defined above and Hal is a halogen atom, e.g. chlorine. It is preferred to use alcohols or alcohol/water mixtures as solvents for this process.

The starting materials of formulae II to VIII are known or, if novel, they can be prepared by methods analogous to known ones and likewise constitute an object of the present invention.

The compounds of formulae I and Ia may be obtained in synthesis as mixtures of different geometric or enantiomeric forms if non-unitary starting materials are employed in the preparation. The mixtures of isomers can be resolved into the individual forms by known methods. A compound of formula I or Ia is to be understood as comprising the individual geometric or enantiomeric forms and the mixtures thereof.

The compounds of formulae I and Ia are suitable for controlling a variety of pests of animals and plants as well as soil pests. The compounds of formulae I and Ia can thus be used for controlling insects, for example of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera and mites and ticks of the order Acarina.

The compounds of formulae I and Ia are particularly suitable for controlling plant-destructive insects in ornamentals and crops of useful plants, in particular in cotton crops (e.g. *Spodoptera littoralis* and *Heliothis virescens*). The compounds of formulae I and Ia are also effective against soil insects (e.g. *Aulacophora femoralis, Chortophila brassicae, Diabrotica balteata, Pachnoda savignyi* and *Scotia ypsilon*). The compounds of this invention are particularly active as ovicides in plant protection, especially for controlling plant-destructive insects, e.g. *Laspeyresia pomonella* and *Lobesia botrana.*

The compounds of formulae I and Ia are also very effective against flies, e.g. *Musca domestica* and mosquito larvae. The compounds of formulae I and Ia are in general distinguished by broad ovicidal and ovolarvicidal activity. They have good activity against ectoparasitic mites and ticks, e.g. of the families Ixodidae, Argasidae and Dermanyssidae, and can inhibit the oviposition of ectoparastic acarids.

The acaricidal and/or insecticidal action can be substantially broadened and adapted to prevailing circumstances by addition of other insecticides and/or acaricides. Examples of suitable additives include: organophosphorus compounds, nitrophenols and derivatives thereof, formamidines, ureas, pyrethroids, carbamates, and chlorinated hydrocarbons.

The good pesticidal activity of the compounds of formulae I and Ia of the present invention corresponds to a mortality of 50 to 60% of the above pests.

Compounds of formulae I and Ia are also combined with particular advantage with substances which exert a synergistic or potentiating effect. Examples of such compounds include: piperonyl butoxide, propynyl ether, propynyl oximes, propynyl carbamates and propynyl phosphates, 2-(3,4-methylenedioxyphenoxy)-3,6,9-trioxaundecane (Sesamex or Sesoxane), S,S,S,-tributylphosphorotrithioate, 1,2-methylenedioxy-4-(2-(octylsulfinyl)propyl)benzene.

The compounds of formulae I and Ia are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions, preparations or mixtures containing at least one compound (active ingredient) of formula I or Ia and, where appropriate, a solid or liquid adjuvant, are prepared in known manner, e.g. by homogeneously mixing and/or grinding the active ingredients with extenders, e.g. solvents, solid carriers, and in some cases surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ethyl acetate, propyl myristate or propyl palmitate, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I or Ia to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ringwood, N.J., 1979, and Dr. Helmut Stache: "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I or Ia, 1 to 99.9% of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients, such as stabilisers, antifoams, viscosity regulators, binders, tackifiers as well as fertilisers or other active ingredients for obtaining special effects.

EXAMPLE 1

(a) Preparation of 4-phenoxyphenoxyacetaldehyde diethyl acetal 150 g of potassium carbonate and 4 g of finely powdered potassium iodide are added to a solution of 112 g (0.6 mole) of 4-phenoxyphenol and 157.6 g (0.8 mole) of bromoacetaldehyde diethyl acetal in 480 ml of dimethylformamide, and the batch is heated, under nitrogen, for 14 hours at 150° C. The salts are then removed by filtration from the reaction solution, and most of the dimethylformamide is distilled off in a water jet vacuum. The residue is dissolved in ether and the resultant solution is washed twice with water, three times with 20% potassium hydroxide solution and again with water. The ethereal solution is then dried over sodium sulfate and the ether is distilled off entirely. The resultant 4-phenoxyphenoxyacetaldehyde diethyl acetal is used without further purification for the preparation of the free aldehyde.

(b) Preparation of 4-phenoxyphenoxyacetaldehyde 280 ml of 1N HCl are added to a solution of 170 g of the acetal obtained in step (a) in 2000 ml of tetrahydrofuran, and the batch is stirred, under nitrogen, for 21 hours at 45° C. Subsequently, the tetrahydrofuran is distilled off in vacuo, the residue is taken up in diethyl ether and the resultant solution is washed repeatedly with saturated sodium bicarbonate solution and finally with water. The ethereal phase is dried over sodium sulfate and the solvent is distilled off entirely. The crude aldehyde is purified by chromatography over silica gel (eluant: a 1:1 mixture of diethyl ether and hexane), affording pure 4-phenoxyphenoxyacetaldehyde with a melting point of 79°–81° C.

(c) Preparation of 4-phenoxyphenoxyacetaldehyde oxime

A solution of 25 g of hydroxylamine hydrochloride and 29.4 g of anhydrous sodium acetate in 100 ml of water is added dropwise at room temperature to a solution of 68.5 g of 4-phenoxyphenoxyacetaldehyde in 300 ml ethanol. After the slightly exothermic reaction has subsided, the mixture is stirred for 2 hours at reflux temperature. The mixture is then cooled to 0° C. and stirred for 3 hours at this temperature, whereupon the resultant oxime crystallises. The crystallised 4-phenoxyphenoxyacetaldehyde oxime is isolated by suction filtration, repeatedly washed thoroughly with water and dried in a vacuum cabinet at 40° C. Melting point: 102°–105° C.

(d) Preparation of 4-phenoxyphenoxyacetaldehyde oxime propargyl ether

With stirring, a solution of 12.2 g of 4-phenoxyphenoxyacetaldehyde oxime in 15 ml of dimethylformamide is added dropwise over about 30 minutes at 0°–5° C. to a suspension of 2.24 g of sodium hydride (55% suspension in mineral oil, which suspension has been washed beforehand with hexane) in 50 ml of dimethylformamide (nitrogen atmosphere). After stirring for a further 4 hours at 8°–10° C., the evolution of hydrogen is complete. Over about 20 minutes, 8.2 g of propargyl bromide are added dropwise at 0°–5° C. to the reaction mixture. Subsequently, the mixture is stirred overnight at room temperature. For working up, the reaction mixture is diluted with water and extracted repeatedly with diethyl ether. The combined ethereal phases are washed with water and dried over sodium sulfate and the solvent is distilled off. Subsequent chromographic purification over 250 g of silica gel (eluant: a 1:9 mixture of diethyl ether and n-hexane) affords the title compound of the formula

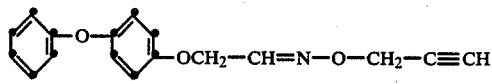

with a refractive index of $n_D^{20°} = 1.5710$ (compound 1).

EXAMPLE 2

(a) Preparation of 4-phenoxyphenoxyacetone oxime

Over about 1 hour, a solution of 22 g of hydroxylamine hydrochloride and 26 g of anhydrous sodium acetate in 110 ml of water is added dropwise at room temperature to a solution of 64 g of 4-phenoxyphenoxyacetone in 260 ml of ethanol. After the slightly exothermic reaction has subsided, the mixture is stirred for a further 3.5 hours at reflux temperature. Subsequently, the ethanol is distilled off from the reaction mixture by rotary evaporation, the aqueous residue is extracted three times with a 2:1 mixture of ether and hexane, the combined organic phases are washed with water and with 10% sodium bicarbonate solution and then dried over sodium sulfate. The solvent is then distilled off. Recrystallisation from a mixture of diethyl ether and pentane affords 4-phenoxyphenoxyacetone oxime with a melting point of 59°–61° C.

(b) Preparation of 4-phenoxyphenoxyacetone oxime ethyl ether

With stirring, a solution of 7.1 g (0.07 mole) of acetone oxime ethyl ether, 12.1 g (0.05 mole) of 4-phenoxyphenoxyacetone and 100 ml of 2N sulfuric acid in 12 ml of 1,2-dimethoxyethane is heated for 12 hours at 80° C., in a weak stream of nitrogen, whereupon the formed acetone distills off. Subsequently, the reaction solution is diluted with 100 ml of ether and the resultant solution is washed three times with 10% sodium bicarbonate solution and twice with water. After drying over sodium sulfate, the solvent is distilled off the crude product is chromatographed over silica gel (eluant: a 19:1 mixture of hexane and ether), affording 4-phenoxyphenoxyacetone oxime ethyl ether (compound 2) of the formula

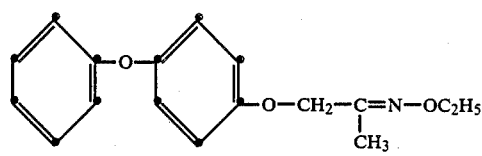

with a refractive index of $n_D^{20°} = 1.5513$.

The following compounds of formula I are prepared in analogous manner:

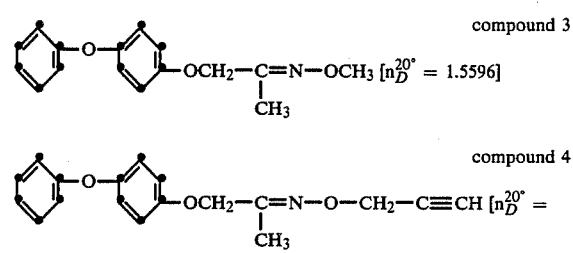

compound 3 compound 4

1.5670]

EXAMPLE 3

Preparation of 4-phenoxyphenoxyacetone oxime N-methyl carbamate

With stirring, a solution of 3.42 g of methyl isocyanate in 10 ml of acetonitrile is added dropwise over 30 minutes at room temperature to a solution of 12.85 g (0.05 mole) of 4-phenoxyphenoxyacetone oxime and 0.05 g of diazabicyclooctane in 90 ml of acetonitrile. After stirring for 7 hours at 40° C., the solvent is distilled off by rotary evaporation and the residue is purified by chromatography over 200 g of silica gel (eluant: a 3:1 mixture of diethyl ether and hexane). The main fraction is subsequently recrystallised in diethyl ether, affording 4-phenoxyphenoxyacetone oxime N-methyl carbamate (compound 5) of the formula

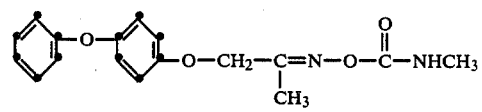

with a melting point of 60°–62° C.

Compound 6 of the formula

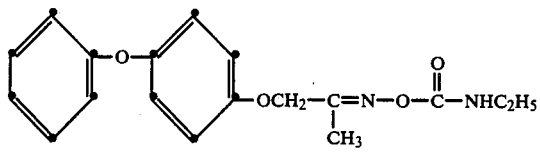

with a melting point of 57°–59° C. is obtained in analogous manner.

EXAMPLE 4

Preparation of 4-phenoxyphenoxyacetone oxime propionic acid ester

With stirring, 5.9 g (0.045 mole) of propionic anhydride are added dropwise over 10 minutes at 60° C. to a solution of 10.3 g (0.04 mole) of 4-phenoxyphenoxyacetone oxime and 0.145 g (0.0012 mole) of 4-dimethylaminopyridine in 30 ml of toluene, and the mixture is stirred for a further 2.5 hours at 60° C. Subsequently, the cooled reaction mixture is diluted with 50 ml of ether and the resultant solution is washed three times with ice-cold 20% sodium carbonate solution. The organic phase is dried over sodium sulfate and the solvent is distilled off. The residue is chromatographed over 200 g of silica gel (eluant: a 1:2 mixture of diethyl ether and n-hexane) and subsequently recrystallised in a 13 mixture of diethyl ether and pentane, affording pure 4-phenoxyphenoxyacetone oxime propionic acid ester of the formula

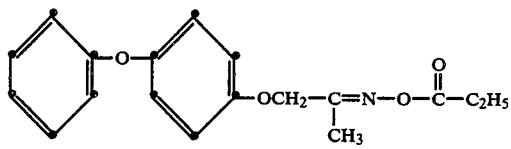

with a melting point of 62°–63° C. (compound 7).

EXAMPLE 5

(a) Preparation of 4-(4-phenoxyphenyl)-2-butanone oxime

Over about 30 minutes, a freshly prepared solution of 15.3 g (0.22 mole) of hydroxylamine hydrochloride in 100 ml of water and 200 ml of 1N sodium hydroxide solution is added dropwise at room temperature to a solution of 48 g (0.2 mole) of 4-(4-phenoxyphenyl)-2-butanone*) in 500 ml of ethanol. Subsequently, the mixture is heated for 1.5 hours at reflux temperature and then stirred for 16 hours at room temperature. The ethanol is distilled off in a water jet vacuum and the residue is extracted repeatedly with ether. The combined ethereal phases are washed repeatedly with water and dried over sodium sulfate and the ther is distilled off entirely. The crude oxime is chromatographed over silica gel (eluant: a 1:1 mixture of diethyl ether and n-hexane). The resultant 4-(4-phenoxyphenyl)-2-butanone oxime melts at 80°–82° C. after recrystallisation in a mixture of diethyl ether and n-hexane.

*) e.g. Helv. Chim. Acta 58, 286 (1975)

(b) Preparation of 4-(4-phenoxyphenyl)-2-butanone oxime propargyl ether 2.57 g of sodium hydride (55% in mineral oil) are washed repeatedly with n-hexane and subsequently suspended, under nitrogen, in 50 ml of tetrahydrofuran. With stirring, a solution of 15 g of 4-(4-phenoxyphenyl)-2-butanone oxime in 80 ml of tetrahydrofuran is added dropwise over 30 minutes at room temperature to the resultant suspension. The mixture is then stirred further at 50° C. until the evolution of hydrogen is complete. A solution of 10.5 g of propargyl bromide in 30 ml of hexamethylphosphoric triamide is then added dropwise at 20° C., and the mixture is stirred for a further 16 hours at room temperature. For working up, first most of the tetrahydrofuran is distilled off by rotary evaporation and the reaction mixture is then diluted with 400 ml of water and the resultant solution is extracted repeatedly with ether. The combined ethereal phases are washed with water and dried over sodium sulfate and the ether is distilled off. Chromatography over silica gel (eluant: a 1:3 mixture of diethyl ether and n-hexane) affords 4-(4-phenoxyphenyl)-2-butanone oxime propargyl ether of the formula

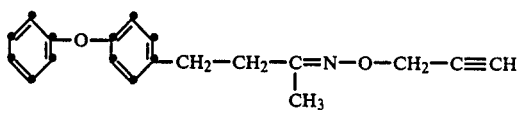

with a refractive index of $n_D^{20°}=1.5647$ (compound 8).

Compound 9 of the formula

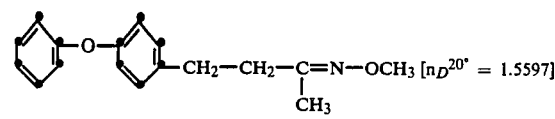

is prepared in analogous manner.

EXAMPLE 6

Preparation of 4-phenoxyphenoxyacetone oxime allyl ether

With stirring, a solution of 7.3 g (0.066 mole) of O-allylhydroxylamine hydrochloride and 5.4 g (0.066 mole) of sodium acetate in 40 ml of water is dropwise over 30 minutes at 35° C. to a solution of 13.3 g (0.055 mole) of 4-phenoxyphenoxyacetone in 70 ml of ethanol. After stirring for a further 4 hours at 35° C., the ethanol is distilled off by rotary evaporation and the residue is extracted repeatedly with diethyl ether. The combined ethereal extracts are washed with 5% sodium carbonate solution and with water, and organic phase is dried over sodium sulfate, the solvent is distilled off and the crude product is purified by chromatography over silica gel (eluant: a 19:1 mixture of n-hexane and diethyl ether), affording the title compound of the formula

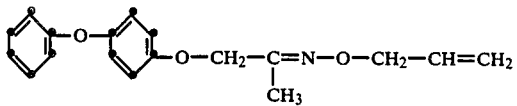

with a refractive index of $n_D^{23}321.5572$ (compound 10).

The compound of the formula

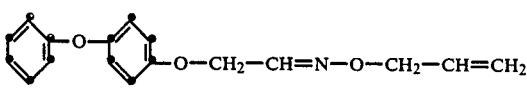

with a refractive index of $n_D^{18} = 1.5633$ (compound 11) is prepared in corresponding manner.

The following compounds of formula I are prepared by procedures analogous to those described in Examples 1 to 6.

| Compound | Structure | Physical data |
|---|---|---|
| 12 | (phenyl)-O-(phenyl)-O-CH$_2$-CH=N-O-C(=S)-NHCH$_3$ | $n_D^{20} = 1.5776$ |
| 13 | (phenyl)-O-(phenyl)-O-CH$_2$-CH=N-O-CH$_2$-CH=CHCl | anti-trans: $n_D^{20} = 1.5700$ <br> syn/cis: $n_D^{20} = 1.5720$ |
| 14 | (phenyl)-O-(phenyl)-O-CH$_2$-CH=N-O-CH$_2$-(methylenedioxyphenyl) | $n_D^{18} = 1.5941$ |
| 15 | (phenyl)-O-(phenyl)-O-CH$_2$-CH=N-O-CH$_2$-(phenyl) | syn: $n_D^{19} = 1.5891$ <br> anti: m.p. = 56–58° C. |
| 16 | (phenyl)-O-(phenyl)-O-CH$_2$-C(CH$_3$)=N-O-C(CH$_3$)$_3$ | $n_D^{33} = 1.5361$ |
| 17 | (phenyl)-O-(phenyl)-O-CH$_2$-C(CH$_3$)=N-O-(CH$_2$)$_3$CH$_3$ | $n_D^{17} = 1.5436$ |
| 18 | (4-F-phenyl)-O-(phenyl)-O-CH$_2$-C(CH$_3$)=N-O-CH$_2$-C≡CH | $n_D^{20} = 1.5640$ |
| 19 | (4-CH$_3$-phenyl)-CH$_2$-(phenyl)-O-CH$_2$-C(CH$_3$)=N-O-CH$_2$-C≡CH | $n_D^{20} = 1.5470$ |
| 20 | (phenyl)-O-(phenyl)-O-(CH$_2$)$_2$-CH=N-O-(CH$_2$)$_5$CH$_3$ | $n_D^{20} = 1.5465$ |

| Compound | Physical data |
|---|---|
| 21 <br> Cl-C₆H₃-O-C₆H₃-S-CH(CH₃)-C(CH₃)=N-O-C₂H₅ | $n_D^{20} = 1.5385$ |

EXAMPLE 7

Formulation Examples for liquid active ingredients of formulae I and Ia according to Examples 1 to 6 (throughout, percentages are by weight)

| 1. Emulsifiable concentrates | (a) | (b) | (c) |
|---|---|---|---|
| compound according to the Preparatory Examples | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | — | 20% |
| xylene mixture | 65% | 25% | 20% |

Emulsions of any required concentration can be produced from such concentrates by dilution with water.

| 2. Solutions | (a) | (b) | (c) | (d) |
|---|---|---|---|---|
| compound according to the Preparatory Examples | 80% | 10% | 5% | 95% |
| ethylene glycol monomethyl ether | 20% | — | — | — |
| polyethylene glycol (mol. wt. 400) | — | 70% | — | — |
| N—methyl-2-pyrrolidone | — | 20% | — | — |
| expoxidised coconut oil | — | — | 1% | 5% |
| ligroin (boiling range 160–190°) | — | — | 94% | — |

These solutions are suitable for application in the form of microdrops.

| 3. Granulates | (a) | (b) |
|---|---|---|
| compound according to the Preparatory Examples | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | (a) | (b) |
|---|---|---|
| compound according to the Preparatory Examples | 2% | 5% |
| highly dispersed silicic acid | 1% | 5% |
| talcum | 97% | — |
| kaolin | — | 90% |

Ready for use dusts are obtained by intimately mixing the carriers with the active ingredient.

Formulation Examples for solid active ingredients of formulae I and Ia according to Examples 1 to 6 (throughout, percentages are by weight)

| 5. Wettable powders | (a) | (b) | (c) |
|---|---|---|---|
| compound according to the Preparatory Examples | 25% | 50% | 75% |
| sodium lignonsulfonate | 5% | 5% | — |
| sodium laurylsulfate | 3% | — | 5% |
| sodium diisobutylnaphthalenesulfonate | — | 6% | 10% |
| octylphenyl polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 6. Emulsifiable concentrates | (a) | (b) |
|---|---|---|
| compound according to the Preparatory Examples | 10% | 10% |
| octylphenol polyethylene glycol ether (4–5 moles of ethylene oxide) | 3% | — |
| calcium dodecylbenzenesulfonate | 3% | — |
| castor oil polyglycol ether (36 moles of ethylene oxide) | 4% | — |
| castor oil thioxilate | — | 25% |
| cyclohexanone | 30% | — |
| butanol | — | 15% |
| xylene mixture | 50% | — |
| ethyl acetate | — | 50% |

Emulsions of any required concentration can be obtained from this concentrate by dilution with water.

| 7. Dusts | (a) | (b) |
|---|---|---|
| compound according to the Preparatory Examples | 5% | 8% |
| talcum | 95% | — |
| kaolin | — | 92% |

Ready for use dusts, are obtained by mixing the active ingredient with the carrier, and grinding the mixture in a suitable mill.

| 8. Extruder granulate | |
|---|---|
| compound according to the Preparatory Examples | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 9. Coated granulate | |
|---|---|
| compound according to the Preparatory Examples | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 10. Suspension concentrate | |
|---|---|
| compound according to the Preparatory Examples | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 8

Insecticidal stomach poison action: *Spodoptera littoralis*

Cotton plants are sprayed with a solution containing 400 ppm of the test compound.

After the spray coating has dried, the plants are populated with larvae of *Spodoptera littoralis* in the $L_1$ stage. Two plants are used per test compound. Evaluation of the mortality rate is made after 2, 4, 24, 48 and 72 hours. The test is carried out at 28° C. and 60% relative humidity. In this test, compounds of formula I according to Examples 1 to 6 exhibit good activity against *Spodoptera littoralis* larvae.

EXAMPLE 9

Action against *Lucilia sericata*

1 ml of an aqueous formulation containing 0.1% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate. In this test, compounds of formula I according to Examples 1 to 6 exhibit good activity against *Lucilia sericata*.

EXAMPLE 10

Action against *Aedes aegypti*

A concentration of 100 ppm is obtained by pipetting a specific amount of a 0.1% solution of the test compound in acetone onto the surface of 150 ml of water in a beaker. After the acetone has evaporated, 30 to 40 two-day-old larvae of Aëdes aegypti are put into the beaker containing the test compound. Mortality counts are made after 2 and 7 days.

Compounds of formula I according to Examples 1 to 6 exhibit good activity in this test.

EXAMPLE 11

Ovicidal action against *Heliothis virescens*

Corresponding amounts of a wettable powder formulation containing 25% by weight of the test compound are mixed with sufficient water to produce aqueous emulsions with active ingredient concentrations of 400 and 200 ppm. One day-old egg deposits of Heliothis on cellophane ® are immersed in these emulsions for 3 minutes and then collected by suction on round filters. The treated deposits are placed in petri dishes and kept in the dark. The hatching rate in comparison with untreated controls is determined after 6 to 8 days. Evaluation is made to determine the minimum concentration of compound required to effect 100% kill of the eggs.

If the above test, compounds 1 and 4 of this invention effect 100% mortality at 200 ppm and 400 ppm respectively.

EXAMPLE 12

Insecticidal contact action against *Myzus persicae*

Pea plants which have been reared in water to a hight of about 4 cm are each populated with about 200 individuals of the species *Myzus persicae* before the start of the test. The treated plants are then sprayed to drip point with an aqueous suspension containing 400 ppm of the test compound. Two plants are used for each compound at its given concentration. A mortality count is made 48 hours after application. The test is carried out at 20°–22° C. and 60% relative humidity.

In this test, compounds of formula I according to Examples 1 to 6 exhibit good activity.

EXAMPLE 13

Action against soil insects (*Diabrotical balteata*)

5 maize seedlings about 1 to 3 cm in length and a disc of filter paper are immersed in an aqueous formulation containing 400 ppm of the test compound. The moist filter paper disc is placed at the bottom of a 200 ml plastic beaker, and then the 5 treated maize seedlings together with 10 larvae of diabrotica balteata in the second to third larval stage are placed in the beaker. Two tests are carried out for each test compound at its given concentration. The beakers containing the larvae are kept for 6 days at daylight, a relative humidity of 40 to 60% and at temperatures of 22° to 24° C. The percentage kill of the test insects is then determined.

In this test, compounds according to Examples 1 to 6 exhibit good activity.

EXAMPLE 14

Action against *Laspeyresia pomonella* (eggs)

Egg deposits of *Laspeyrasia pomonella* not more than 24 hours old are immersed on filter paper for 1 minute in an aqueous acetonic solution containing 400 ppm of the test compound.

After the solution has dried, the eggs are placed in petri dishes and kept at a temperature of 28° C. The percentage of larvae hatched from the treated eggs is evaluated after 6 days.

Compounds 2, 3 and 4 of the invention are 100% effective in this test.

EXAMPLE 15

Action against *Spodoptera littoralis* (feeding inhibition, repellent action)

Leaf discs of 4 cm diameter are prepared from cotton leaves. Some of the discs are treated by being immersed in an aqueous formulation of the test compound and subsequently dried. A rectangular flat container (10×20 cm) is populated with 50 Spodoptera larvae in the second larval stage. The container is sealed with a plastic lid in which there are two round slots (diameter: about 7 cm). Each slot is covered with a plastic beaker such that the aperture of the beaker is flush with the periphery of the slot. On the bottom of each beaker there is an agar layer with a cotton leaf disc stuck on it. The one beaker contains a treated disc and the other an untreated disc.

After 18 days at room temperature and with neon lighting, an evaluation is made of feeding inhibition (no feeding damage on the treated disc) and of repellent action (no larvae on the treated disc) taking the phototactic behaviour of the test larvae into consideration.

In this test, compound 10 of the invention effects 100% feeding inhibition and exhibits 100% repellent action at 200 ppm.

EXAMPLE 16

Action against ticks (Inhibition of oviposition)

Fully replete females of the cattle tick Boophilus microplus are used as test animals. 10 ticks of an OP-resistant strain (e.g. Biarra strain) and 10 ticks of a normally sensitive strain (e.g. Yeerongpilly strain) are treated at each given concentration. The ticks are affixed to plates to which double-sided adhesive tape has been applied. The ticks are then either wetted with aqueous emulsions of solutions of the test compounds or brought into contact with a cotton swab which has been impregnated with one of these liquids. The ticks are subsequently kept in a climatised chamber under constant conditions. Evaluation is made three weeks later. The total inhibition of the deposit of fertile eggs is determined.

The inhibiting activity of the substances is expressed as the minimum concentration of substance in ppm to achieve 100% activity against normally sensitive and resistant adult female ticks.

In this test, 100% acaricidal activity is exhibited by compounds 2, 4 and 10 at 250 ppm and by compounds 1, 11, 13 and 14 at 500 ppm.

What is claimed is:

1. A compound of formula

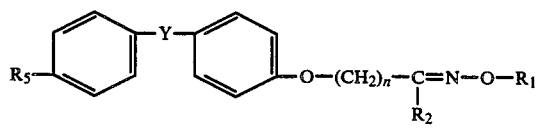

wherein
$R_1$ is $C_1-C_6$alkyl, $C_2-C_5$alkenyl, $C_3$monohaloalkenyl or $C_3-C_5$-alkynyl;
$R_2$ is hydrogen or methyl;
$R_5$ is hydrogen, fluorine, chlorine or methyl;
n is 0 or 1 and
Y is oxygen, sulfur or

2. A compound of claim 1, wherein n is 1.
3. A compound of claim 1, wherein Y is oxygen.
4. A compound of claim 1 wherein $R_5$ is fluorine, chlorine or methyl.
5. The compound according to claim 3 of the formula

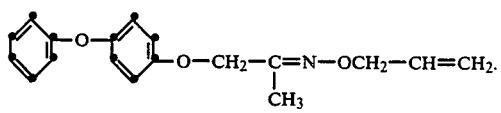

6. The compound according to claim 3 of the formula

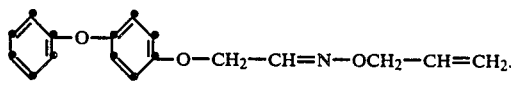

7. The compound according to claim 3 of the formula

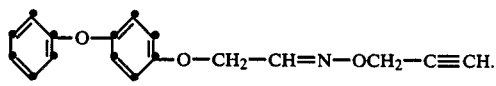

8. The compound according to claim 3 of the formula

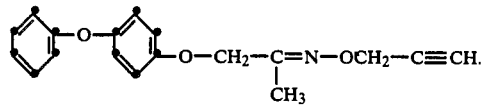

9. The compound according to claim 3 of the formula

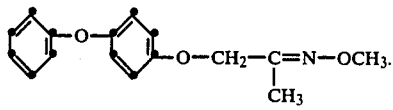

10. The compound according to claim 3 of the formula

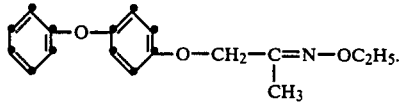

11. The compound according to claim 3 of the formula

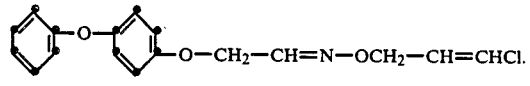

12. A pesticidal composition which comprises, as active ingredient, an insecticidally or acaricidally effective amount of a compound according to claim 1, together with a carrier and/or adjuvant customarily employed in the art of pesticide formulation.

13. A method of controlling pests of animals selected from insects and acarides, which method comprises applying to said animals or to the locus thereof an insecticidally or acaricidally effective amount of a compound according to claim 1.

14. The method according to claim 13 for controlling insects of animals.

15. The method according to claim 14 for controlling eggs of plant destructive insects.

16. A method of controlling pests of plants selected from insects and acarides, which method comprises applying to said plants or to the locus thereof an insecticidally or acaricidally effective amount of a compound according to claim 1.

17. The method according to claim 16 for controlling insects on plants.

18. The method according to claim 17 for controlling eggs of plant destructive insects.

* * * * *